US008060220B2

(12) United States Patent
Liebergesell et al.

(10) Patent No.: US 8,060,220 B2
(45) Date of Patent: Nov. 15, 2011

(54) PROMOTION OF ORAL HYGIENE AND TREATMENT OF GINGIVITIS, OTHER PERIODONTAL PROBLEMS AND ORAL MAL ODOR WITH ALTERNATING CURRENT WAVEFORMS AND DEVICE THEREFOR

(75) Inventors: Sachiko Liebergesell, Darien, CT (US); William G. Eppler, Jr., Norwalk, CT (US)

(73) Assignee: Sachiko Liebergesell, Darien, CT (US)

( * ) Notice: Subject to any disclaimer, the term of this patent is extended or adjusted under 35 U.S.C. 154(b) by 1149 days.

(21) Appl. No.: 11/499,033

(22) Filed: Aug. 4, 2006

(65) Prior Publication Data

US 2006/0271148 A1 Nov. 30, 2006

Related U.S. Application Data

(63) Continuation-in-part of application No. 10/634,590, filed on Aug. 5, 2003, now abandoned.

(51) Int. Cl.
*A61N 1/36* (2006.01)

(52) U.S. Cl. ............... 607/134; 607/46; 607/47; 607/76

(58) Field of Classification Search ............ 607/68, 607/46, 66, 51, 47, 134, 50, 76
See application file for complete search history.

(56) References Cited

U.S. PATENT DOCUMENTS

| 2,004,751 | A |   | 6/1935 | Fischer et al. ............... 307/106 |
| 4,109,660 | A |   | 8/1978 | Nesmeyanov et al. ......... 607/47 |
| 4,509,519 | A |   | 4/1985 | Detsch ............................ 607/51 |
| 4,550,733 | A |   | 11/1985 | Liss et al. ....................... 607/47 |
| 4,676,257 | A |   | 6/1987 | Halpern ......................... 607/134 |
| 4,924,880 | A | * | 5/1990 | O'Neill et al. .................. 607/47 |
| 6,230,052 | B1 | * | 5/2001 | Wolff et al. ...................... 607/2 |
| 6,584,359 | B1 |   | 6/2003 | Motoi ............................. 607/76 |

* cited by examiner

*Primary Examiner* — Niketa Patel
*Assistant Examiner* — Alyssa M Alter
(74) *Attorney, Agent, or Firm* — Ohlandt, Greeley, Ruggiero & Perle, LLP; George W. Rauchfuss, Jr.

(57) ABSTRACT

A method for promoting oral hygiene and treating a patient for gingivitis, other periodontal problems, or oral mal odor by transmitting to the gums of a patient electrical current waveforms of electrical voltage within the range of from about ±0.1V to about ±3.9V as a combination of ultra-weak electrical currents.

10 Claims, 5 Drawing Sheets

PROMOTION OF ORAL HYGIENE AND TREATMENT OF GINGIVITIS, OTHER PERIODONTAL PROBLEMS AND ORAL MAL ODOR WITH ALTERNATING CURRENT WAVEFORMS AND DEVICE THEREFOR

RELATED APPLICATION

This application is a continuation-in-part application of U.S. patent application Ser. No. 10/634,590, filed Aug. 5, 2003 now abandoned.

FIELD OF THE INVENTION

This invention relates to a method of promoting oral hygiene and treating gingivitis, other periodontal problems and oral mal odor in a patient in need thereof, which process applies very weak electrical stimulation to the oral cavity of a patient to promote oral hygiene and treat gingivitis, other periodontal problems and oral mal odor, and it also relates to a device suitable for providing such specific alternating current waveforms to the oral cavity such that the electrical stimulation has a therapeutic and/or prophylactic effect for promoting oral hygiene and against gingivitis, other periodontal problems and oral mal odor in the patient.

BACKGROUND OF THE INVENTION

The hard and soft tissues of the mouth are covered with microbial populations that contain bacteria with different metabolic capabilities. The Gram-positive bacteria within these microbial populations readily catabolize carbohydrates to produce acids which attack the hard tissues of the oral cavity, resulting in the formation of dental caries lesions or cavities. In contrast, the Gram-negative bacteria, especially the anaerobes readily metabolize various amino acids contained in salivary and, to lesser extent, other peptides and proteins in the oral cavity to form end-products which favor the formation of oral malodor and periodontitis. This process of peptide, protein and amino acid degradation by the mouth bacteria is referred to as oral bacterial putrefaction. The mixture of malodorous compounds produced by the Gram-negative anaerobic bacteria during putrefactive degradation of proteins, peptides and amino acids include hydrogen sulfide, methyl mercaptan, and dimethyl sulfide (formed from the sulfur containing amino acids cysteine, cystine and methionine); indole and skatole (formed during the metabolism of tryptophan); cadaverine and putrescine (produced from lysine and ornithine); and butyrate and valerate (produced from the metabolism of other amino acids). The production of these malodorous compounds in the oral cavity results in a condition commonly referred to as oral malodor. It is estimated that about 75% of all adults have some form of this condition.

Hydrogen sulfide, methyl mercaptan, butyrate and propionate are putrefaction end-products that also have cell and tissue altering non-inflammatory roles in the periodontitis process. Hydrogen sulfide and methylmercaptan are compounds particularly effective in facilitating the oral epithelium penetrability of toxins and other large molecular weight compounds produced by Gram-negative bacteria, and leading to the inflammation and tissue degradation characteristics of gingivitis and periodontitis. Gingivitis is a condition in which the gingiva is red, swollen and bleeding. If left untreated, gingivitis may develop into periodontitis, a condition characterized by destruction of the periodontium, including epithelial attachment loss, periodontal membrane and ligament destruction, and loss of gingiva and alveolar bone. Severe periodontitis resulting in deep periodontal pockets may ultimately result in tooth loss.

Adult periodontal disease is a widespread medical problem that is difficult to treat, especially in the middle-aged and elderly. It develops when bacteria indigenous to the oral cavity colonize gingival sulci, forming bacterial plaques in the absence of oral hygiene. Inflammation (gingivitis) develops and eventually spreads, causing tooth attachment loss (periodontitis). The diversity of the oral flora, the chronic nature of the disease, and the absence of a generally accepted animal or in vitro model, have made the molecular pathogenesis of this disease by bacteria difficult to study. Therapies for this disease have also been hampered by ignorance of the bacterial induction process. Current therapy requires that the dentist improve oral hygiene by debridement (scaling and root-planing) and repair tissue architecture using periodontal surgery as necessary. The patient must undertake regular toothbrushing and flossing. This therapy is expensive, time-consuming and unpredictable in its outcome.

Previous studies have largely otherwise focused on the use of germicidal agents to treat gingivitis-periodontitis and oral malodor. Recent findings have recognized that gingivitis-periodontitis and oral malodor arise from a common process, oral bacterial putrefaction.

Both gingivitis and periodontitis are inflammatory diseases caused by plaque formation on the teeth. Chronic periodontitis often leads to destruction of the tissues supporting the teeth. Plaque can be defined as a soft bacteria-containing coating on the surface of a tooth. When a tooth is not clean, plaque formation will commence and this will lead to gingivitis in the gingival area.

The inflammation of the gingiva leads to the formation of the gingival sulcus, and a gingival pocket is formed. Clear evidence that plaque is responsible for gingivitis was derived from the induction of experimental gingivitis (H. Loe et al., J. Periodontology 36: 177-187, 1965). Starting from a state of clinical gingival health, all participants developed gingivitis within 10 to 21 days after elimination of oral hygiene procedures. After reinstating plaque control, the gingiva returned to a normal condition within seven days.

Gingivits is characterizered by swelling and redness of the free gingival margin. Bleeding is caused by, for example, toothbrushing and gentle probing by a dentist. There is a loss in the connective tissue tone, which tends to open the gingival sulcus. The disease process may be combatted by either eliminating the plaque or by altering the environment by changing the composition of the plaque.

In order to colonize a surface, bacteria must be able to adhere to the surface in question. The mucous epithelium of the oral cavity is constantly renewed, so that bacteria adhering to the mucosal surface will tend to be sloughed off together with the outer layer of dead cells of the epithelium, thus preventing bacterial invasion of the living tissue underneath the dead epithelial cells. On the other hand, the dental surface constitutes a firm non-living base to which bacteria effectively adhere. The bacterial colonies on the dental surface (plaque), especially at the gingival margin and in the subgingival region, are not removed by any similar process, resulting in an antibacterial immune reaction from the surrounding tissue evident as a chronic inflammation of the gingival tissue. Under normal and healthy conditions this inflammatory reaction is mild, with a delicate balance being struck between colonizing bacteria and antibacterial effect.

Inflammation of the gingiva due to bacterial colonization of the dental surfaces is therefore an important initial stage of periodontitis. If the bacterial colonies (plaque) are not removed, accumulation of bacteria along the gingival margin or in the dento-gingival region will lead to increased gingival inflammation and destruction of the periodontal membrane possibly followed by bone resorption. Eventually a periodontal pocket develops in which more bacteria accumulate, resulting in increased inflammation and infection proper of the tissue so as to lead to a more pronounced degradation of the tooth-supporting tissue.

Wherever there is a plaque-coated surface, calcium ions can take part in chemical reactions, giving rise to formation of calculus. Calculus can be found on the tooth surface as supragingival or subgingival deposits. These deposits must be removed in order to maintain normal gingival conditions.

A characteristic of periodontal infection is that once bacteria/plaque have established themselves (i.e. infected) firmly in a periodontal pocket, the natural humoral defense mechanisms are not capable of dealing with the infection, and the plaque may turn into hard deposits, i.e. calculus.

Apart from the general inflammation caused by the presence of bacteria/plaque, the release of hydrolytic enzymes like hyaluronidase, desoxyribonuclease, collagenase and proteases probably contributes to the destruction of dental tissue.

The severity of tissue damage probably depends on the antigen/antibody reaction of the organism as well as the degree of retention of inflammatory products in the periodontal pockets. Accumulation of mediators of local inflammation accelerates the process. In most cases the process is slow, with immunoinfiltration of the gingival tissue and formation of granulation tissue which contains inflammatory cells. Occasionally, this slow progression is superseded by acute exacerbations with accumulation of inflammatory cells and release of lysosomal enzymes. Such exacerbations are probably due to changes in the bacterial flora.

Juvenile periodontitis differs from the above marginal periodontitis only by an early onset, and by often involving certain groups of teeth and being accompanied by a much lesser degree of plaque formation. It begins in late childhood, resulting in a pronounced loss of the teeth's supporting tissue, and it too is an infectious disease on a par with other periodontal diseases.

Current periodontal therapy is directed towards the removal of bacterial plaque and calculus deposits—subgingival and supragingival plaque. These goals are usually achieved by means of scaling and polishing, instruction in oral hygiene procedures, periodontal surgery where indicated and periodic maintenance.

Another option for treatment, which remains to be fully evaluated, is the possibility of disrupting the subgingival microflora in such a way that supragingival plaque control becomes less important. One potential approach to such a treatment is intensive intermittent disruption using local or systemic antimicrobial agents, examples of which are metronidazole, tetracycline and erythromycin. Such agents may also be used for irrigation of the periodontal pockets. The potential effect is based on the concept that alteration of the subgingival microflora at appropriate intervals may be sufficient to prevent the development of an ecosystem suitable to the reestablishment of pathogens in adequate levels for disease initiation. Another approach is bacterial substitution, replacing potential pathogens with bacteria which occupy the same ecological niche but have a reduced pathogenic potential.

Still another approach is the use of chemical agents which will alter plaque and subgingival microflora sufficiently to prevent gingivitis or the development of gingivitis into parodontitis.

A vast number of chemical agents have been evaluated as potential antiplaque/antigingivitis agents. The first generation agents are antibacterial agents with limited effectiveness. These agents are effective as antibacterials in vitro, but are either not retained intra-orally or they are rapidly released. Therefore, they inhibit the bacteria for a short period of time, after which time bacteria growth is resumed. Their clinical effect is limited unless the agents are used frequently, i.e. four to six times a day. This group includes topical antibiotics, oxygenating compounds, quaternary ammonium compounds, phenolic compounds, and sanguinarine. The second generation agents are effective not only in vitro but also in vivo, due to their retention and release kinetics. At present, chlorhexidine and chlorhexidine analogues are the primary second generation compounds, and stannous fluoride may also qualify as belonging to this group.

Penicillin, tetracycline, erythromycin, polymyxin B, kanamycin, metronidazole and spiromycin have been used for anti-plaque treatment. However, the potential for the development of bacterial resistance and hypersensitivity reactions should limit the use of antibiotics for plaque control purposes. In general, antibiotics may hold great promise for specific bacterial diseases in the oral cavity, but they appear to be inappropriate for the routine control of supragingival plaque and associated diseases.

Quaternary ammonium compounds are cationic surface agents which are capable of reducing surface tension, absorbing to negatively charged surfaces and disrupting membranes. Plaque reducing effects have been reported with benzethonium chloride and cetylpyridinium chloride at 0.1%, when used four times daily. Side effects with quaternary ammonium compounds have included both ulcerations and discomfort.

Phenolic compounds have a long history of use in the oral cavity as either a mouthwash or as throat lozenges. A commercial preparation (Listerine®) of thymol, eucalyptol, methyl salicylate, benzoic acid and boric acid has shown a certain plaque reducing effect as compared to a placebo. It is not clear whether the degree of plaque inhibition due to this agent is of long-term value in the prevention of periodontitis.

Sanguinarine, a benzophenanthradine alkaloid, has recently been reported to be potentially useful as a plaque control agent. Preliminary studies indicate that sanguinarine is capable of providing some reduction and prevention of plaque and gingivitis.

Chlorhexidine gluconate in 0.1-0.2% solutions and 1% gels have been shown to exert an effective plaque inhibiting and anti-gingivitis effect, when used short-term. A few long-term studies with chlorhexidine gluconate have also shown promising effects against plaque formation. The oral use of chlorhexidine has been associated with staining of the teeth and tongue and a bitter taste, and longer use often gives rise to alterations of the mucosa. Owing to the cationic nature of the compound, it is difficult to mask the taste by addition of flavoring agents without affecting the biological activity. Other agents such as alexidine and octenidine are structurally similar to chlorhexidine, and appear have a comparable effect.

In summary, treatment of gingivitis and periodontitis has mainly been prophylactic, emphasizing the importance of removing calculus and dental plaque and generally improving oral hygiene by mechanical means such as toothbrushing using fluoride-containing toothpastes etc., and using dental floss, toothpicks and the like. When necessary, surgical methods have been used in order to reduce the depth of the periodontal pockets. Systemic or topical antibacterial treatment with tetracyclin or the like has also been shown to have some effect, especially during acute infectious episodes, and finally, irrigating or rinsing the mouth with antiseptics such as chlorohexidine has been shown to exert a certain, if limited, effect, especially on gingivitis and plaque formation. However, none of these treatments are entirely satisfactory as they either require a high degree of patient compliance and/or do not possess a high degree of efficiency.

There is therefore a need to provide an effective method for promoting oral hygiene and treatment, either prophylactic or therapeutic treatment, of gingivitis, other periodontal problems and oral mal odor.

SUMMARY OF THE INVENTION

The objective of this invention is to provide to the gums of a person, as appropriate from the perspective of promotion oral hygiene and treatment of gingivitis, other periodontal problems and oral mal odor, the voltage of a stimulating alternating electrical current waveform and wherein the promotion oral hygiene and treatment of gingivitis, other periodontal problems and oral mal odor are obtained by means of such electrical stimulation.

In one aspect, the invention provides a method for promotion of oral hygiene and treating a patient for gingivitis, other periodontal problems and oral mal odor, the method comprising transmitting to the gums of a patient electrical current waveforms of alternating electrical voltage within the range of from about ±0.1V to about ±3.9V, preferably from about ±0.3V to about ±3.9V, and more preferably from about ±0.3V to about ±1.3V, as a combination of ultra-weak electrical currents that are comprised of a single type of current waveform or a combination of multiple types of current waveforms made up of alternating current square-waves of differing patterns, such that there is applied to the gums a low electrical current of 500 µA or less in order to promotion oral hygiene and provide treatment of the patient for the effects of gingivitis, other periodontal problems and oral mal odor.

In another aspect, the invention provides a device for providing a method for promotion oral hygiene and treating a patient for gingivitis, other periodontal problems and oral mal odor, wherein the device comprises an electrical output apparatus in the nature of an electrical control device and a pair of disposable electrical conductive elements for electrical communication to said electrical output apparatus device and suitably designed for insertion into the oral cavity of a patient, the pair of electrical conductive elements contain an electrical conductive amount of an electrical conductive material such that the electrical resistance of the electrical conductive elements is 1 kΩ or less and whereby electrical current waveforms similar to the biological electrical currents that occur in the human body are adapted to provide an electrical effect to the gums of the patient by contacting the gums with the electrical conductive elements that conduct electricity from the electrical output apparatus through the electrical conductive elements to the gums of the patient, and wherein said electrical control device is adapted to repeatedly output an electrical voltage within the range of from ±0.1V to about ±3.9V, preferably from about ±0.3V to about ±3.9V, and more preferably from about ±0.3V to about ±1.3V, to said electrical conductive elements as a combination of ultra-weak electrical currents that are comprised of a single type of current waveform or a combination of multiple types of current waveforms made up of alternating current square-waves of differing patterns, such that when said electrical conductive elements come into contact with the gums of the patient, said flexible elements pass through and apply to the gums a low electrical current of 500 µA or less in order to promote oral hygiene and provide treatment of the patient for the effects of gingivitis, other periodontal problems and oral mal odor.

A treatment in which the device in accordance with this invention is used, is performed by putting both electrically conductive elements, with which good electrical conductivity is obtained by means of including electrically conductive material, such as, for example, silver or copper, onto the opposite sides of the gums of a patient in need of oral hygiene improvement and treatment for possible gingivitis, other periodontal problems and oral mal odor. The electrically conductive elements are used by placing them in electrical communication with an electrical output apparatus (electrical output and control device) that outputs alternating current waveform electrical currents that yield the appropriate electrical stimulation effect to the gums. The electrical conductive elements may be placed in electrical communication with the electrical output apparatus by means of electrical connection cords or by means of a remote transmitters that receive the electrical signals from the electrical output apparatus.

The minute electrical current of the alternating current with which it is possible to obtain effects on the gums of the oral cavity of the patient is made possible by means of conducting electrical stimulation that is supplied from an electric current stimulation device to the above-described electrically conductive elements. Such alternating currents may be composed of a plural number of alternating currents of square-waves that are serially combined alternating current square-waves of differing patterns or alternating currents of waves that are of a single pattern.

For the stimulation that results from passing electricity, this invention may pass electrical current of waveforms that can essentially be considered to be of a single waveform, or rather, as described above, combines alternating current square-wave of differing patterns, and thereby provides the therapeutic and prophylactic effect for promoting oral hygiene and against possible gingivitis, other periodontal problems and oral mal odor in the mouth of the patient.

Either the single alternating current waveform or the plural number of varieties of alternating current waveforms from the repetitive combination of differing alternating current square-waves patterns, types of waveforms, and the further repetitive combination of the alternating current waveform combinations is effective to promote oral hygiene and provide treatment against possible gingivitis, other periodontal problems and oral mal odor in the mouth of the patient.

The electrical conductive elements that are to contact the gums of a patient may be in any form suitable for insertion into the patient's mouth to permit the electrical current waveform to be applied to the gums of a patient. One example of the electrical conductive elements may be in the form of a pair of conductors having terminals that are electrically conductive, to which electrically conductive flexible sheet pad elements can be attached and detached at will, so as to be capable of discharging electrical current when the said electrically conductive flexible sheet pad elements come into contact with gums of a patient.

In one embodiment of the invention the method and device employs the use of a single type of alternating current waveform., In another embodiment the electrical current waveform of alternating electrical voltage transmitted to the gums of the patient comprises a combination of ultra-weak electrical currents that are comprised of a combination of multiple types of current waveforms made up of alternating current square-waves of differing patterns. For example, the alternating current waveforms are such that when the positive side electric potential level and the negative side electric potential level are indicated with the reference electric potential as the mid-point, the alternating current waveforms described above should be formed by the repetitive combination of one of the two electric potential levels and the indication of the other level the electric potential levels indicated once in an alternating square-wave pattern as a single pattern for the time interval of the 1st reference time as a single pattern, and the repetition of the afore-described single pattern thrice as the triple repetitive pattern, and the indication of the afore-described reference electric potential for twice the time of the 1st reference time as the pause, in the sequence of the afore-described triple repetitive pattern, the afore-described pause, the afore-described triple repetitive pattern, the afore-described pause, the afore-described single pattern, the afore-described pause, the afore-described single repetitive pattern, the afore-described pause, the afore-described single pattern, the afore-described pause, the afore-described single pattern and the afore-described pause.

As another way there are repetitive combinations of alternating current square-waves of the indication of one of the two electric potential levels indicated for the time of the 2nd reference time and the indication of the electric potential level of other for ½ of the time of the 2nd reference time as the 1st repetitive pattern and the alternating current square-waves of the indication of one of the afore-described electric potential levels for ½ of the time of the time of the afore-described 2nd reference time and the indication of the afore-described reference electric potential for ½ of the time of the time of the afore-described 2nd reference time and the indication of the other of the afore-described electric potential levels for ½ of the time of the afore-described reference time as an alternating current square-wave and the afore-described reference electric potential for ½ of the time of the time of the afore-described 2nd reference time as the pause, in the sequence of the afore-described 1st repetitive pattern, the afore-described pause, the afore-described 2nd repetitive pattern, the afore-described pause, the afore-described 2nd repetitive pattern, the afore-described pause, the afore-described 2nd pattern and the afore-described pause.

Or another way would be repetitive patterns of alternating current square-wave of the indication of one of the levels of the electric potential levels for the time of the 3rd reference time and the indication of the other level of afore-described electric potential levels for the time of the afore-described 3rd reference time and the indication of the other level of the afore-described electric potential levels for the time of the afore-described 3rd reference time and the indication of the other level of the afore-described the electric potential levels for the time of the afore-described 3rd reference time and the indication reference electric potential for twice the time of the afore-described 3rd reference time and the indication of the level of the afore-described one of the electric potential levels for ¼ of the time of the afore-described 3rd reference time and indication of the afore-described reference electric potential for ½ of the time of the afore-described 3rd reference time and indication of the one of the levels of the afore-described electric potential levels for ¼ of the time of the afore-described 3rd reference time and the indication of the levels of the afore-described reference electric potential for the time of the 3rd reference time and the indication of the other level of the afore-described the electric potential levels for ¼ of the time of the afore-described 3rd reference time and the indication of the reference electric potential for ½ of the time of the afore-described 3rd reference time and the indication of the other level of the afore-described electric potential levels for ¼ of the time of afore-described 3rd reference time and indication of the afore-described reference electric potential for the time of the afore-described 3rd reference time as the 3rd repetitive pattern of the alternating current square-wave, and the indication of the afore-described reference electric potential for the time of the afore-described 3rd reference time and the indication of the afore-described one of the levels of the electric potential levels for ¼ of the time of the afore-described reference time and the indication of the reference electric potential for ½ of the time of the afore-described 3rd reference time and the indication of the afore-described other level of the electric potential levels for ¼ of the time of the afore-described 3rd reference time as the repetitive pattern in one direction, and the indication of the reference electric potential for the time of the afore-described 3rd reference time and the indication of the afore-described other level of electric potential levels for ¼ of the time of the afore-described 3rd reference time and the indication of the reference electric potential for ½ of the time of the afore-described 3rd reference time and the indication of the afore-described other level of electric potential levels for ¼ of the time of the afore-described 3rd reference time as the repetitive pattern in the other direction and indication of the afore-described reference time for the time of the afore-described reference time as the pause, in the sequence of the afore-described 3rd repetitive pattern, the afore-described 3rd repetitive pattern, the afore-described repetitive pattern in one direction, the afore-described repetitive pattern in the other direction, the afore-described pause, the afore-described repetitive pattern in one direction, the afore-described repetitive pattern in the other direction, the afore-described pause, the afore-described repetitive pattern in one direction, the afore-described repetitive pattern in the other direction, the afore-described pause, the afore-described repetitive pattern in one direction.

Furthermore, when the waveform composed of the repetition of each of the above-described 3 specific waveform types is used by further repeating the combination, from an effect perspective, the results may be superior to those obtained when each of the specific waveforms was used singularly. Regarding the combination these 3 specific waveform types, it was confirmed that effective results can be obtained by setting the 2nd reference time to be quadruple the time of the afore-described 1st reference time and the afore-described 3rd reference time to be equal to the time of the afore-described 1st reference time.

Such a composition of the alternating current waveforms of this invention is such that it as similar as possible to the biological electrical current that occurs in live human bodies, and the electrical current should be a very weak one so that the operator will not be exposed to any danger as well as for the safety of the gums of the patient. For example, the voltage should be from about ±0.1 to about ±3.9 V, preferably from about ±0.3 to about ±3.9 V and the electrical current stimulation should be applied under electrical conductivity conditions of 500 μA or less. While the device of this invention can provide a voltage of from about ±0.1 to about ±3.9 V, still more preferably ±0.3 to about ±1.3V the device is provided with an appropriate voltage selection switch so as to provide a selected range of voltage for sensitive gum areas and a higher selected range of voltage for a less sensitive gum areas. As a further example, one or more switches should provide a voltage of within the range of from about ±0.3 to about ±1.3 V at one setting, and a voltage within the range of from about ±1.3 to about ±3.9 V for a second setting, and the electrical current stimulation should be applied under electrical conductivity conditions of 500 μA or less. Preferably, the electrically conducting, flexible pads have a conducting material such that the electrical resistance of the electrical conducting, flexible pads is 1 kΩ or less. In a preferred embodiment of the invention the device of the invention is adapted to repeatedly output the selected electrical voltage in a cycle time of about 12.8 seconds.

The nature of the treatment device that is in accordance with this invention is such that it can be used for daily or weekly gum care by the simple use of electrical stimulation that is based on the use of the alternating current waveforms on the gums, the nature of which is described above. For example, the electrically conductive elements are in electrical communication, such as by way of a hard wire connection or through a wireless remote transmitter or the like, with an electrical current stimulation device that outputs very weak electrical currents in alternating current waveforms that have the desired promotion of oral hygiene and anti gingivitis, other periodontal conditions or oral mal odor effect that has been explained in the above description.

When the switch for the electrical current control device is turned ON, the required electrical current is output to the electrically conductive elements that have been inserted into the oral cavity of the patient so as to be in contact with the opposite side of the patient's gums such that; by this, the electrical current described above passes to the gums, and treatment is applied as the electricity is conducted, with the objective of prophylactically and therapeutically promoting oral hygiene and treating gingivitis, other periodontal problems and/or oral mal odor conditions in the oral cavity of the patient.

BRIEF DESCRIPTION OF THE DRAWINGS

The invention will be described in reference to the accompanying drawings in which.

DETAILED DESCRIPTION OF INVENTION AND PREFERRED EMBODIMENTS

Figure 1:
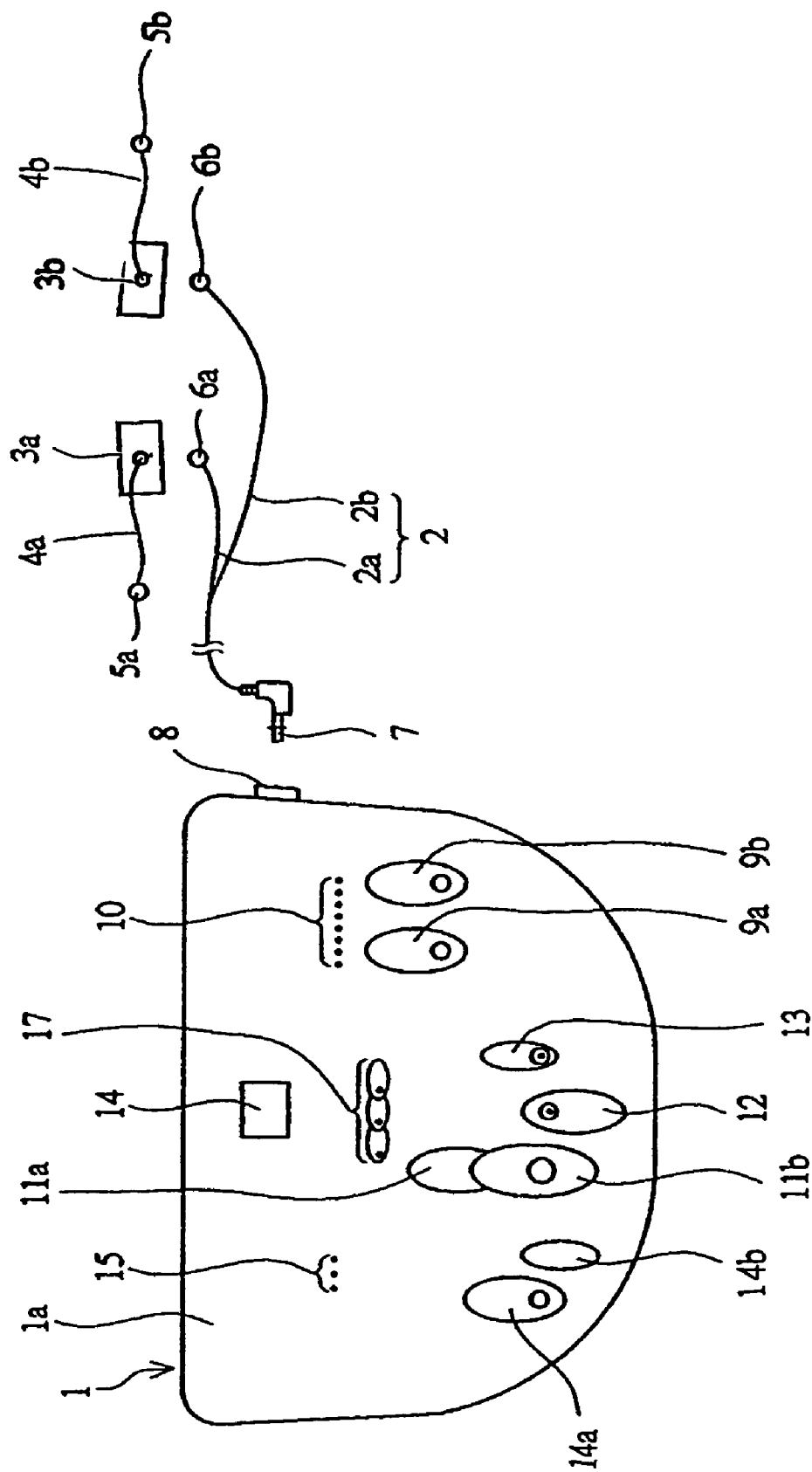
FIG. 1 is an explanatory diagram that depicts the general nature of the treatment device in accordance with one embodiment of this invention.
Figure 2:
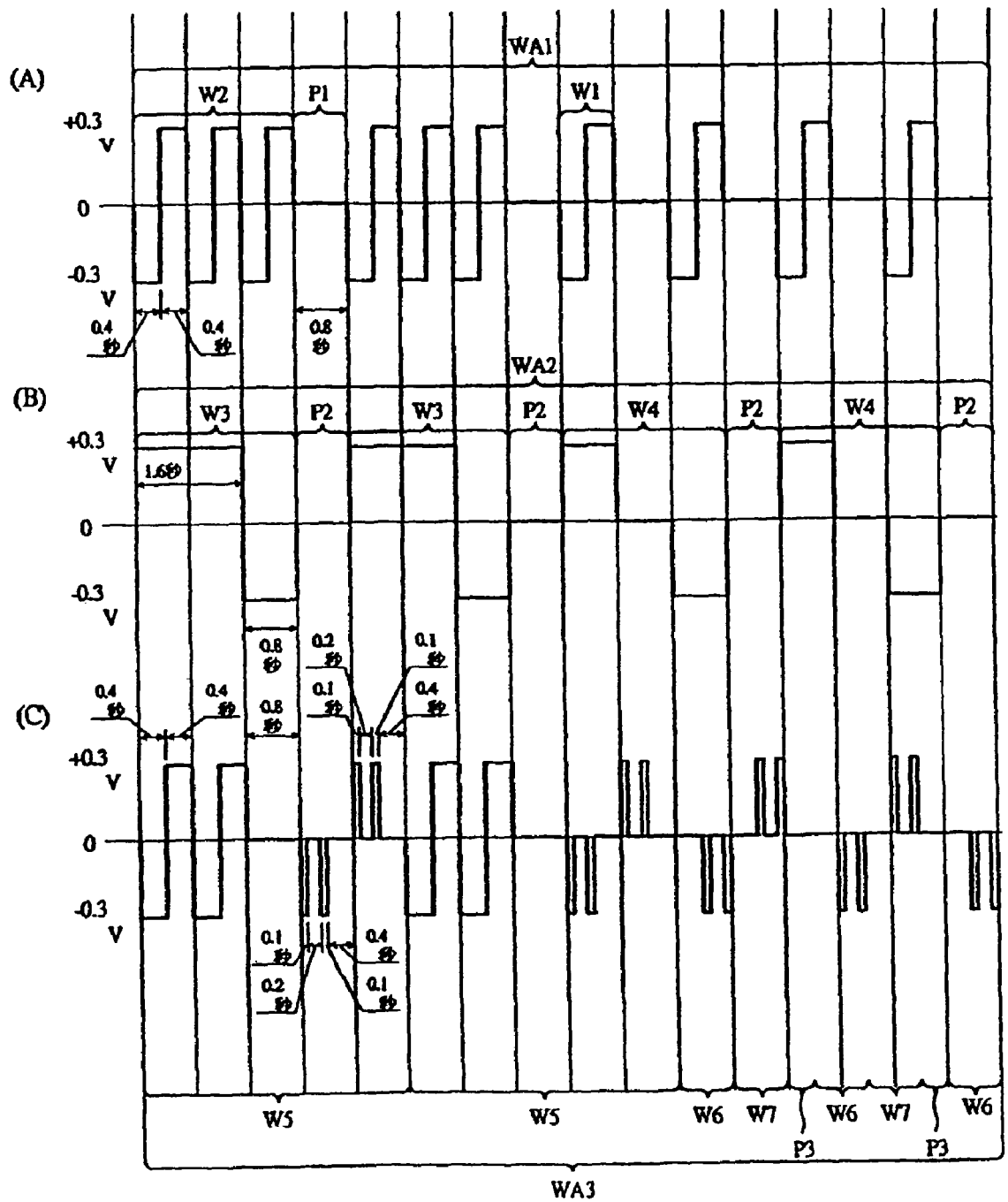
FIGS. 2 (A), (B) and (C) are each diagrams that depict one example of one cycle of the alternating current waveforms used in the treatment method in accordance with this invention.
Figure 5:
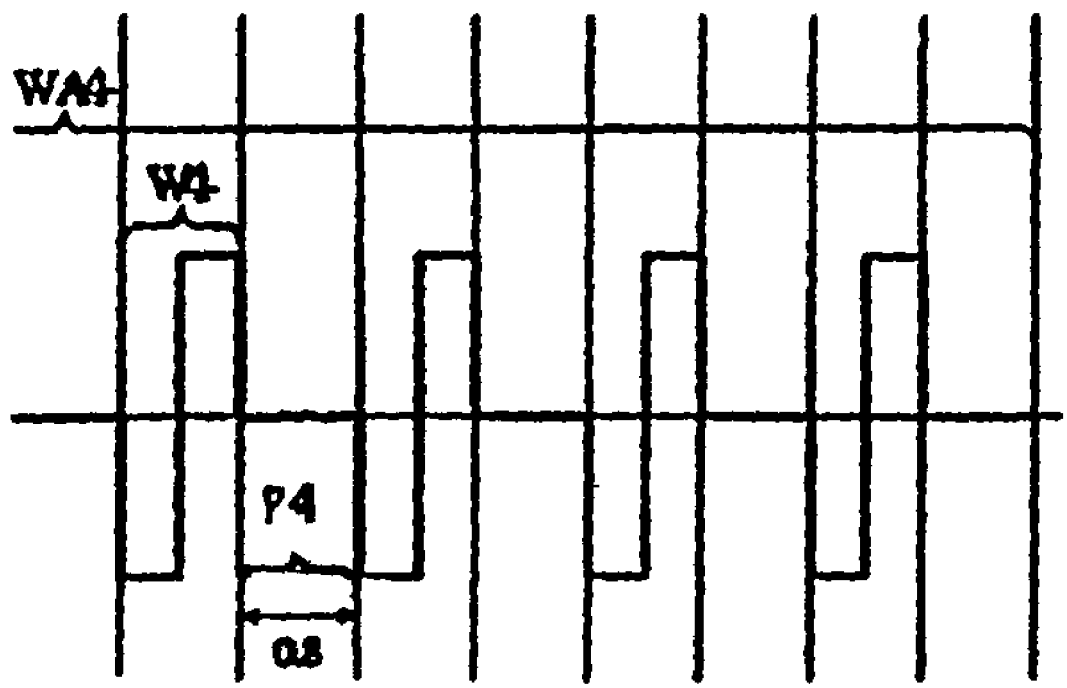
FIG. 5 is a diagram that depicts one example of an alternating current waveform that may be used as the sole waveform employed in the treatment method in accordance with this invention.

A exemplary, but non-limited, treatment device useful in the method of this invention is composed of an electrical current output apparatus (electrical control apparatus) 1, a connection cord 2 and a pair of electrically conductive, flexible sheet pad elements, 3a and 3b as shown in FIG. 1. The electrical control apparatus can be powered by either AC or DC current source, including being battery powered. Within the electrical current control device 1, is built-in an electrical current controller circuit that is not depicted in the figures; for example, it is possible to control the output voltage so as to repetitively combine the alternating current waveforms of the same or differing patterns in order to produce a single or a plural number of alternating current square-waves, that are then subjected to further repetitive combining output very weak electrical current in the form of the alternating current waveforms such as the plural number of alternating current square waves that are depicted in FIG. 2 or the single alternating current square wave that is depicted in FIG. 5. Such a treatment device can be for example a device marketed for cosmetic treatment of the skin by Saya Wavetech, Inc. of Darien, Conn., under the trademark MIRACLE WAVE®.

The operation panel 1a is established for the electrical current control device 1, may be as depicted in FIG. 1. On this operational panel 1a have been established a touch type main switch 14a for turning the device ON and a main switch 14b for turning it OFF. By engaging the main switch 14a for turning the device ON, the device is rendered into a state in which it is possible to output very weak electrical current in alternating waveform to the electrical current control device 1. In this state, the electrically conductive, flexible pad elements 3a and 3b are connected to the electrical current control device 1 by means of the connection cord 2

The electrically conductive flexible pad elements 3a and 3b are both made of any suitable material, such as for example, a thin flexible plastic sheet such as MYLAR®, TEFLON® or the like, that contains a conductivity material, such as for example, silver or copper, in an amount to render the pads electrically conductive to the gums in the oral cavity of a patient. By means of including a conductivity material, it is possible to impart good conductivity to the flexible pad elements 3a and 3b. The quantity of conductive material that is contained in the pad elements should be such that the electrical resistance of the electrically conductive flexible pad elements is generally about 1 k$\Omega$ or less. The pad elements 3a and 3b can be of any suitable size or shape suitable for fitting into the oral cavity of a patient and contacting the gums of the patient.

By means of using silver as described above, when compared to using a conductive material that has a lower conductivity, such as copper, it is possible to reduce the voltage load of the alternating current that is conducted to the electrically conductive, flexible pad elements 3a and 3b, and it is possible to keep low the over all electric potential used to achieve stimulation by conducting electricity.

Also, by means of the use of silver as a conductive material, as compared to when carbon is used as a conductivity material, it is possible by means of the anti-bacterial characteristics of the silver that is used as a conductivity material, to protect the electrically conductive flexible pad elements from bacterial growth of various bacteria that are apt to adhere on the flexible pad elements. The choice of an appropriate metal will generally depend on its bacteriostatic properties and the conductivity and toxicity of the compounds it may form in contact with the mouth chemistry.

The above-described composition of the electrically conductive flexible pad elements 3a and 3b is designed with terminals 5a and 5b that serve the role of connecting the electrically conductive flexible pad elements 3a and 3b via lead lines 4a and 4b to the connecting cord 2. The connecting cord 2 has a pair of lead lines, 2a and 2b, for the electrically conductive flexible pad elements 3a and 3b. At one end of the lead line pair, 2a and 2b, there are lead line terminals 6a and 6b to be connected to terminals 5a and 5b on lead lines 4a and 4b of the electrically conductive flexible pad elements 3a and 3b such that the flexible pad elements can to be connected/disconnected at will to the device 1. The other end of the lead lines 2a and 2b are both connected to a common jack 7 for electrical attachment to the electrical control device 1. The terminals 5a, 5b 6a and 6b can be, for example, any suitable combination of male and female connectors that permit ready connection of terminals 5a and 5b to terminals 6a and 6b.

It is preferred that the pads 3a and 3b along with their lead lines 4a and 4b with terminals 5a and 5b constitute a disposable unit so that a sterile or clean unit can be used for each patient and for each treatment.

By means of connecting the jack 7 of the connection cord 2 to the output terminal 8 of the electrical current control device 1, the alternating currents of the plural number of varieties of alternating current waveforms that result from the repetitive combination of the alternating current square-waves of differing patterns and the further repetitive combination thereof to form the alternating current waveforms that are depicted on FIG. 2 are supplied to the electrically conductive flexible pad elements 3a and 3b.

With the electrical current control device 1, it is possible to change the range of the voltage of the alternating currents that are generated. For example, it is possible to switch between two alternating currents in the range of about ±1.3V to ±3.9 V. Each system is furthermore capable of changing the voltage in a plural number of stages. In terms of these systems, the electrical stimulation that is applied should be is selected according to what is appropriate for the gums of the patient to which it being applied. For patients with gums that are sensitive, the smaller of the above-described voltages range systems should be used and for the gums of a patient whose gums are not so sensitive and the patient is able to withstand a higher voltage, the higher voltage range system (for example that which is of a scope that is approximately 3 times that of the lower voltage scope) can be used. Most generally, the lower voltage range system with a voltage with the range of ±0.3 V to ±1.3V will be employed for most patients. As depicted in FIG. 1, the composition is such that the switching can be accomplished with eight levels shown by lead lamps 10.

On the operational panel 1a of the electrical current control device 1, a volume up switch 9a with which the voltage is raised one level at a time, and a volume down switch 9b with which the voltage is lowered one level at time have been established. A light emitting diode (LED) level lamp 10 has been established to indicate what is the prevailing voltage setting that can show each of the levels to which the 30 voltage can be switched. It is possible to know what is the prevailing voltage level from which light emitting diode is lit.

Also, when setting which voltage system is to be used, when it is to be set so that is appropriate for gums of a patient, a lower voltage range of about (±0.1V to about ±1.3V) select switch 11a and a higher voltage range of from about ±1.3V to about ±3.9V) select switch 11b have been established for the mode selection.

A timer start/end switch 12 and a timer set switch 13 have been established. With the timer set switch 13, for example, it is possible to set the duration time for one of three settings, such as for example 10 minutes, 15 minutes or 20 minutes. After setting the duration using the timer switch 13, it is possible to engage the timer start/end switch 12. If the timer start/end switch 12 is engaged after it has been initially engaged, the timer will disengage in the mid course. The duration that has been selected appears on the timer indicator window 14, and the composition is such that it is possible to know how much time is left from the digital display.

The electrical current control device 1 in accordance with this invention is such that it is possible to operate the device by means of the rechargeable built-in battery as an electrical power source. By using an adapter for recharging with alternate currents in a manner such that one end is connected to the electrical current control device 1 and the other end is connected to a household use electrical power source plug outlet, the built-in battery is charged making it possible to operate the device. To serve a gauge for seeing how much electrical charge remains in the battery, a battery checker 15 has been established; the prevailing situation is indicated by means of color differentiated light emitting diodes.

Figure 3:
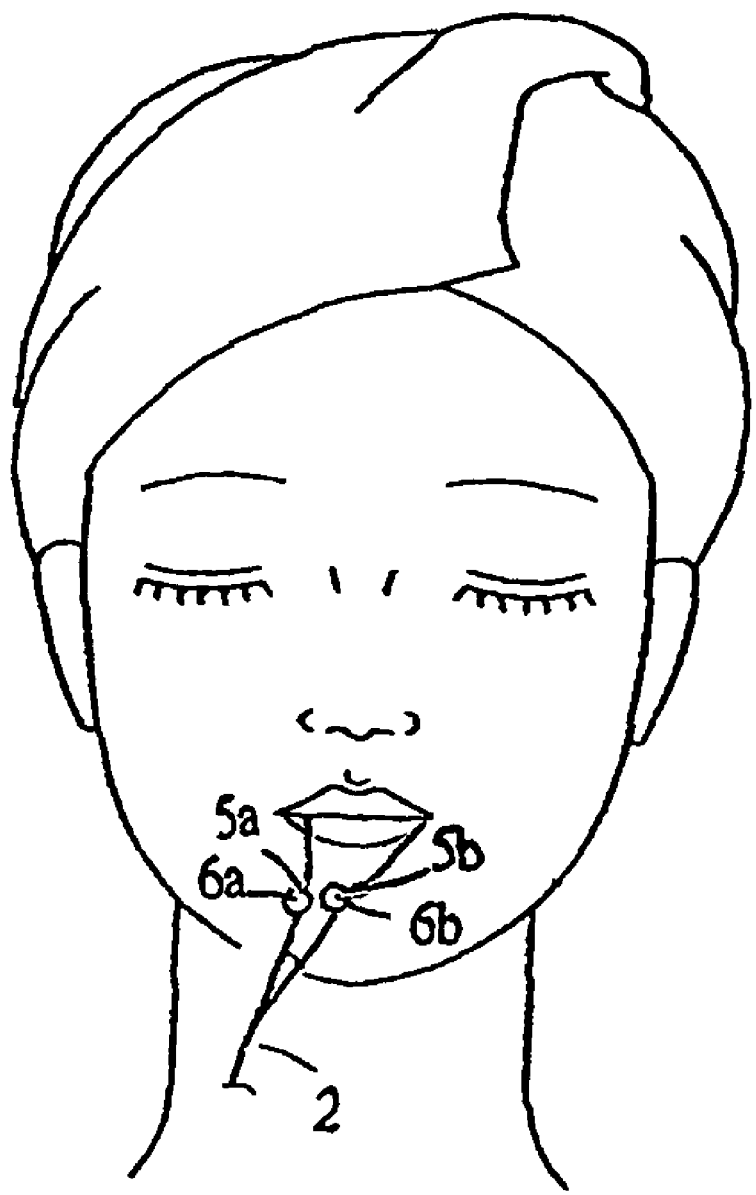
FIG. 3 depicts an oral gum treatment given in accordance with this invention.

The device in accordance with this invention is used in the following manner. First of all, as is depicted in FIG. 1, the terminals 5a and 5b of lead lines 4a and 4b of the pads 3a and 3b are each connected to a terminal 6a and 6b of the lead lines 2a and 2b, then both pad elements 3a and 3b are placed in the oral cavity of a patient, on opposite side of the gums as depicted in FIG. 3. Although as in the afore-described, extremely weak output voltage does go through the electrically conductive flexible pad elements 3a and 3b, but in order to assure ample electrical conductivity, it is a good idea to wet the electrically conductive flexible pad elements 3a and 3b with a liquid such as distilled water that has good electricity conduction characteristics.

On the other hand, at the connection point of the output terminal 8 of the electrical current control device 1, the lead lines 2a and 2b of the connection cord 2 to which the jack 7 has been inserted are hooked up in advance to the terminals 5a and 5b of the electrically conductive flexible pad elements 3a and 3b in order to prepare the electrically conductive flexible pad elements 3a and 3b for conducting electricity.

Under such conditions, the main switch 14a for turning the device ON is engaged, and then the either switch 11a or the switch 11b is selected and engaged in is accordance with the treatment that is about to be given. At the same time, as required, the setting level for the output voltage may be changed.

If the output voltage is to be changed, the volume up switch 9a or the volume down switch 9b is engaged. In the event that the main switch 14b for turning the device OFF has been engaged and the use of the treatment device has been concluded, the device is designed in such a way that at the electrical current control device 1, the output voltage will automatically be set once more at the lowest possible setting, thus making it unnecessary to confirm the setting for the voltage when starting to use the device. The device is designed in such a manner that even if a high voltage setting is the last one used, that high voltage setting will not be generated when the device is used the next time.

In the treatment of the gums, as has been outlined in the above description wherein it is desired to employ a combination of differing waveforms, in one embodiment it is desirable to use any one of the alternating current square waves WA1, WA2, WA3 or a combination of the differing alternating current square-waves patterns, as et forth in FIG. 2 and as described more fully hereinafter.

For use alternating current waveform WA1, when the level of the positive side electric potential and the level of the negative side electric potential are indicated with the reference electric potential as the mid-point, the alternating waveforms should be composed a single pattern W1 in which is one of the levels of the two electric potential levels and the other level of the two electric potential levels for the time of the 1st reference time in an alternating manner, and a triple repetitive current pattern W2 that consists of a triple repetition of the single pattern W1, and a pause P1 that is composed of the indication of the reference electric potential for twice the time of the afore-described 1st reference time in a repetitive combination sequence of the triple repetitive current pattern W2, the pause P1, the triple repetitive current pattern 2, the pause P1, the single pattern W1, the pause P1, the single pattern W1, the pause P1, the single pattern W1, the pause P1, the single pattern W1 and the pause P1.

In particular, in cases such as depicted in FIG. 2 (A), when the above-described 1st reference time is set at 0.4 second, which is to say that for an interval of 0.4 second, one of the levels of the two electric potential levels and the other level of electric potential levels are indicated in an alternating manner once to form a single pattern W1, and a triple repetitive pattern W2 wherein the single pattern is repeated thrice, and a pause 1 wherein the reference electric potential is indicated for 0.8 seconds in the repetitive combination sequence of the triple repetitive current pattern W2, the pause 1, the triple repetitive current pattern W2, the pause 1, the single pattern W1, the pause P1, the single pattern W1, the pause P1, the single pattern W1, the pause P1, the single pattern W1 and the pause P1.

The alternating current waveform WA1 that is described above is a waveform in which the above-described series combination is repeated in cycles of 12.8 seconds. By means of the repetition of this alternating current waveform WA1, while the very weak electrical current is being conducted, the preparatory treatment for the gums of the patient that is outlined in the above description should be conducted.

The use of alternating current waveform WA2 is one in which when the electric potential level of the positive side and the electric potential level of the negative side are indicated with the reference electric potential as the mid-point, the alternating current waveform should consist of the indication of one of the levels of the two electric potential levels for the time of the 2nd reference time and the indication of the other of the electric potential levels for ½ of the time of the 2nd reference time as the 1st repetitive pattern W3 of the alternating current square-waves, and one of the levels of the two electric potential levels for ½ of the time of the 2nd reference time and the indication of the reference electric potential for ½ of the time of the 2nd reference time and the indication of the other of the electric potential levels for ½ of the time of the 2nd reference time as the 2nd repetitive pattern W4 of the alternating current square-waves, and the indication of the standard electric potential for ½ of the time of the 2nd reference time as pause P2, in the repetitive combination sequence of the first repetitive pattern W3, the pause P2, the first repetitive pattern W3, the pause P2, the 2nd repetitive pattern W4, the pause P2, the 2nd repetitive pattern W4 and the pause P2.

In the situation that is depicted in FIG. 2 (B), for the above-described alternating current waveform WA2, the 2nd reference time has been set at 1.6 seconds. This means that the alternating current waveform WA2 that is depicted in FIG. 2 (B) is that for which when the level of the electric potential on the positive side and the level of the electric potential on the negative side are indicated with the reference electric potential as the mid-point, the level of one of the afore-described two electric potential levels is indicated for 1.6 seconds, and the other electric potential is indicated for 0.8 seconds as the 1st repetitive pattern W3 of the alternating current square-waves, and the standard electric potential is indicated for 0.8 seconds and the level of the afore-described other electric potential level is indicated for 0.8 seconds as the 2nd repetitive pattern W4 of the alternating current square-waves, and the indication of the reference electric potential for 0.8 seconds forms the pause P2, in the repetitive combination sequence of the first repetitive pattern W3, the pause P2, the first repetitive pattern W3, the pause P2, the 2nd repetitive pattern W4, the pause P2, the 2nd repetitive pattern W4 and the pause P2.

The cycles of the alternating current waveform WA2 in which this series of alternating current square-wave patterns are combined is also composed in such a way that the cycle is 12.8 seconds as is the case with the above-described alternating current waveform WA1, and the treatment should also be conducted repeatedly during the specified time with this alternating current waveform WA2.

For alternating current waveform WA3, the alternating current waveforms should be such that when the electric potential level of the positive side and the electric potential level of the negative side are indicated with the reference electric potential as the mid-point, one of the electric potential levels is indicated for the time of the 3rd reference time and the other level of the electric potential levels is indicated for the time of the 3rd reference time and one of the electric potential levels is indicated for the time of the 3rd reference time and the other level of the electric potential levels is indicated for the time of the 3rd reference time and the reference electric potential is indicated for twice the time of the 3rd reference time and one of the electric potential levels is indicated for ¼ of the time of the 3rd reference time and the reference electric potential is indicated for ½ of the time of the 3rd reference time and the other level of the electric potential levels is indicated for ¼ of the time of the 3rd reference time and the reference electric potential is indicated for the time of the 3rd reference time and the other level of the electric potential is indicated for ¼ of the time of the 3rd reference time and the reference electric potential is indicated for ½ of the time of the 3rd reference time and the other level of the electric potential levels is indicated for ¼ of the time of the 3rd reference time and the reference electric potential is indicated for the time of the 3rd reference time as the 3rd repetitive pattern W5 of the alternating current square-waves, and the reference electric potential is indicated for the time of the 3rd reference time and one of the electric potential levels is indicated for ¼ of the time of the 3rd reference time and the reference electric potential is indicated for ½ of the time of the 3rd reference time and one of the electric potential levels is indicated for ¼ of the time of the 3rd reference as the one directional repetitive pattern W6, and the reference electric potential is indicated for the time of the 3rd reference time and the other level of the electric potential levels is indicated for ¼ of the time of the 3rd reference time and the reference electric potential is indicated for ½ of the time of the 3rd reference time and the other level of the electric potential levels is indicated for ¼ of the time of the 3rd reference time as the other direction repetitive pattern W7, and the reference electric potential is indicated for the time of the 3rd reference time as pause P3 in the repetitive combination sequence of the 3rd repetitive pattern W5, the 3rd repetitive pattern W5, the one directional repetitive pattern W6, the other directional repetitive pattern W7, the pause P3, the one directional repetitive pattern W6, the other directional repetitive pattern W7, the pause P3 and the one directional repetitive pattern W6.

In the case of that which is depicted in FIG. 2 (C), in the above-described alternating current waveforms, the situation is that for the above-described 3rd reference time, the same 0.4 second setting is used as with the afore-described 1st reference time which means that one of the levels of the afore-described two electric potential levels is output for 0.4 seconds and the afore-described other electric potential level is output for 0.4 seconds and one of the levels of the afore-described electrical potential levels is indicated for 0.4 seconds and the afore-described other electric potential level is output for 0.4 seconds and the afore-described reference electric potential is indicated for 0.8 seconds and one of the levels of the afore-described electric potential levels is output for 0.1 second and the above-described reference electric potential is output for 0.2 second and one of the levels of the afore-described electric potential levels is output for 0.1 second and the afore-described reference electric potential is indicated for 0.4 seconds and the afore-described other electric potential level is indicated for 0.1 second and the afore-described reference electric potential is indicated for 0.2 second and the afore-described other electric potential level is indicated for 0.1 second and the afore-described reference electric potential is indicated for 0.4 second as the 3rd repetitive pattern W5 of the alternating current square-waves, and the afore-described reference electric potential is indicated for 0.4 second and one of the levels of the afore-described electric potential levels is indicated for 0.1 second and the afore-described reference electric potential is indicated for 0.2 second and one of the levels of the afore-described electric potential levels is indicated for 0.1 second as the one directional repetitive pattern W6, and the afore-described reference electric potential is indicated for 0.4 second and the afore-described other electric potential level is indicated for 0.1 second and the afore-described reference electric potential is indicated for 0.2 second and the afore-described other electric potential level is indicated for 0.1 second as the other directional repetitive pattern W7, and the afore-described reference electric potential is indicated for 0.4 second as the pause P3 in a repetitive combination sequence of the 3rd repetitive pattern W5, the 3rd repetitive pattern W5, the one directional repetitive pattern W7, the other directional repetitive pattern W6, the pause P3, the one directional repetitive pattern W6, the other directional repetitive pattern W7, the pause P3, and the other directional repetitive pattern W7. The alternating current waveform WA3 too is repeated for its designated cycle of 12.8 seconds, and within the time allotted for the conducting electricity that is based on this alternating current waveform, the above-described treatment should be conducted.

In order to output the above-described three differing alternating current waveforms WA1, WA2 and WA3, after the alternating current waveform WA1 has been repeatedly output for the designated cycle time of 12.8 seconds from the electrical current control device 1, the design is such that there is an automatic output change by which the alternating current waveform WA2 is output. After that, there is the waveform output by which the alternating current waveform WA2 is repeatedly output for the designated cycle time of 12.8 seconds, and after that, there is an output change so that the alternating current waveform WA3 is automatically output. Then the alternating current waveform WA3 is repeatedly output for the designated cycle time of 12.8 seconds, and after this waveform output, the output is automatically stopped.

The changes in the above-described alternating current waveforms WA1, WA2 and WA3 should be used in the gum treatment, in which case, if the total is to take 15 minutes, then each of the 3 types of treatments can be conducted for 5 minutes each.

The output changes of the above-described combined alternating current waveforms WA1, WA2 and WA3 can be confirmed by means of the wave lamp 17 that is composed of three light emitting diodes (LEDs) that serve to correspond to each of the alternating current waveforms; by checking it [the wave lamp], it is possible to confirm which form is currently being output, thus making it possible to conduct the appropriate treatment.

In the explanation of the above description, as has been depicted in FIG. 2, the combination alternating waveforms WA1, WA2 and WA3 each have their electric potential set at ±0.1 V but it is permissible to change the voltage within eight levels that range from ±0.1 V to ±1.3 V. The range of the changes in voltage should be, for example, in the approximate range of 0.1 to 0.2 V.

Figure 4:
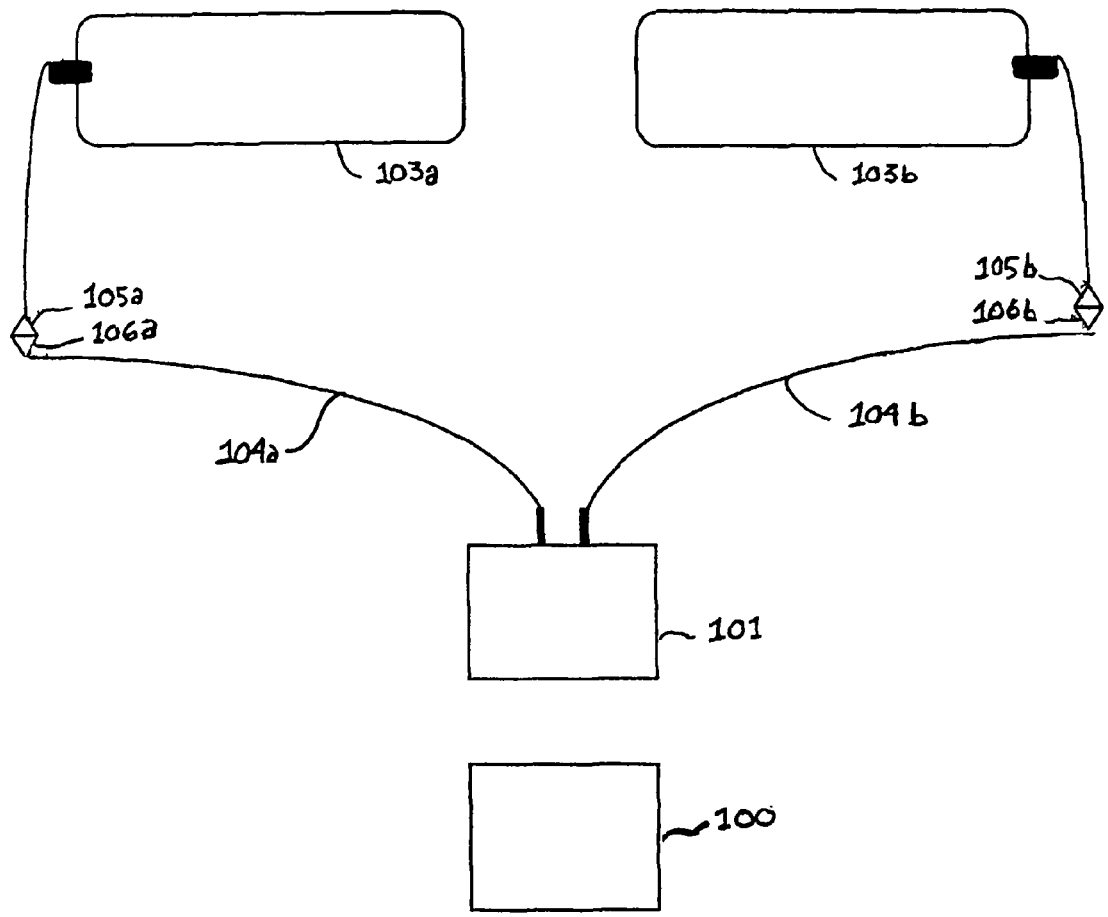
FIG. 4 is an explanatory block diagram that illustrates the general nature of a further treatment device in accordance with another embodiment of this invention.

It will be understood that the above-described device is merely illustrative of, but not limited to, a device capable of providing the requires electrical stimulation to the gums of a patient to promote oral hygiene and treat the patient for the effects of gingivitis, other periodontal problems and/or oral mal odor, and that any device capable of providing or transmitting to the gums of a patient electrical current waveforms of electrical voltage within the range of from about ±0.1V to about ±3.9V as a combination of ultra-weak electrical currents that are comprised of either a single or a combination of multiple types of current waveforms made up of alternating current square-waves of differing patterns, such that there is applied to the gums a low electrical current of 500 µA or less in order to promote oral hygiene and provide treatment of the patient for the effects of gingivitis, other periodontal problems and oral mal odor, can be employed in the treatment method of this invention. Previous paragraphs have described the use of a combination of waveforms. In FIG. 5 there is illustrated a single waveform that may be output by a device As stated previously, it is only necessary that the electrically conductive elements be in electrical communication with the electrical control apparatus and need not be hard wired connected. As illustrated in FIG. 4 the electrical connection can be by means of a remote wireless transmitter. In FIG. 4 an electrical control apparatus 100 outputs the electrical voltage in the desired, selected waveform format to a remote transmitter 101 that transmit the voltage through a pair of electrically conducting connector elements 104a and 104b, such as cables, to electrical conducting elements 103a and 103b, such as electrical conductive flexible sheet pads suitable shaped and sized for insertion into a patient oral cavity and so as to be in electrical contact with the patients gums. The electrical conducting elements 103a and 103b are preferably disposable elements. For purposes of permitting the electrical conducting elements 103a and 103b to be disposable and easily replaceable these elements 103a and 103b and connector elements 104a and 104b may be provided with complimentary connecting elements 105a and 105b and 106a and 106b, respectively, such as complimentary male and female button receptacles. With these complimentary connecting elements disposable electrical conducting elements 103a and 103b may be readily replaced for each user of the device.

In another embodiment of this invention the alternating current waveform employed may be a single alternating current waveform, i.e., a series of the same alternating current waveform. Such a single alternating current waveform WA4 is illustrated in FIG. 5. For use alternating current waveform WA4, when the level of the positive side electric potential and the level of the negative side electric potential are indicated with the reference electric potential as the mid-point, the alternating waveforms should be composed a single pattern W1 in which is one of the levels of the two electric potential levels and the other level of the two electric potential levels for the time of the 1st reference time in an alternating manner.

In particular, in cases such as depicted in FIG. 5, a pause P4 wherein the reference electric potential is indicated for 0.8 seconds in the repetitive combination sequence of the triple repetitive current pattern W4.

As an example of the method of this invention, a MIRACLE WAVES®device of the type described in FIG. 1 was employed and is illustrated in FIG. 3. As shown in this FIG. 3, the flexible pad elements 3a and 3b (not shown) have been inserted inside the oral cavity of the patient in contact with the opposite sides of the patient's gums and are connected to the connecting cord 2 via terminals 5a, 5b, 6a and 6b, which connecting cord is plugged into the device 1 (not shown). An oriental woman of approximately age 63 years was diagnosed by a periodontist as having gingivitis-periodontitis and oral mal odor, with deep periodontal pockets. After that diagnosis, the woman received the following treatment of her gums once a week for a period of five weeks, namely there was provided to her gums electrical current waveforms of electrical voltage of about ±0.76V as a combination of ultra-weak electrical currents that are comprised of a combination of multiple types of current waveforms made up of alternating current square-waves of differing patterns, such that there was applied to the gums a low electrical current of 500 µA. After this weekly treatment for five weeks, there was no evidence of gingivitis, or other periodontal problems or oral mal odor and the oral hygiene of her oral cavity was significantly improved.

It will be appreciated that various part of the device and method may be combined in any suitable manner to obtain the purposes of this invention. For examples the device of FIG. 1 can be made to output either the multiple waveform of FIG. 2 or the single waveform of FIG. 5 and either type of waveform transmissions may be conducted to the patient's oral cavity by a wired device like FIG. 1 or with a wireless device as illustrated in FIG. 4.

While the invention has been described herein with reference to the specific embodiments thereof, it will be appreciated that changes, modification and variations can be made without departing from the spirit and scope of the inventive concept disclosed herein. Accordingly, it is intended to embrace all such changes, modification and variations that fall with the spirit and scope of the appended claims.

We claim:

1. A method for promoting oral hygiene, treating a patient for gingivitis and other periodontal problems, or oral mal odor, the method comprising placing into an oral cavity of a patient in need of any such treatment electrically conductive, disposable pads contacting opposite sides of the patient's gum and transmitting to the gums of the patient an electrical current waveform of alternating electrical voltage such that there is applied to the gums a low electrical current of 500µA or less in order to provide treatment of the patient for promoting oral hygiene and combating the effects of gingivitis, other periodontal problems, or oral mal odor, and wherein the electrical current waveform of alternating electrical voltage transmitted to the gums of the patient comprises a combination of ultra-weak electrical currents that are comprised of a combination of multiple types of current waveforms made up of alternating current square-waves of differing patterns.

2. A method according to claim 1 for promoting oral hygiene, treating a patient for gingivitis, other periodontal problems, or oral mal odor, wherein the electrical current waveform of alternating electrical voltage transmitted to the gums of the patient comprises an electrical current waveform of electrical voltage within the range of from about ±0.1V to about ±3.9V.

3. A method according to claim 2 for promoting oral hygiene, treating a patient for gingivitis, other periodontal problems, or oral mat odor, wherein the electrical current waveform of alternating electrical voltage transmitted to the gums of the patient comprises an electrical current waveform of electrical voltage within the range of from about ±0.3V to about ±3.9V.

4. A method according to claim 1, for promoting oral hygiene, treating a patient for gingivitis, other periodontal problems, or oral mal odor, wherein said alternating current waveforms are provided with a 1st reference electric potential as a mid-point of an electric potential level on a positive side and the electric potential level on a negative side,
repetitive alternating current waveform combinations are provided by repetitively combining the said alternating current waveforms provided as a single pattern in an alternating current square-wave pattern in a manner such that one level of the two electric potentials is provided and then, in turn, another electric potential is provided for the time of a 1st reference time, and a triple consecutive pattern in which the said single pattern is continued three times, and a pause for twice the time of the said 1st reference time
in the sequence of the said triple consecutive pattern, the said pause, the said triple consecutive pattern, the said pause, the said single pattern, the said pause, the said single pattern, the said pause, the said single pattern, the said pause and the said single pattern, the said pause.

5. A method according to claim 1, for promoting oral hygiene, treating a patient for gingivitis, other periodontal problems, or oral mal odor, wherein the said alternating current waveforms are provided with a reference electrical potential as a mid-point of the electrical potential level on the positive side and the electric potential level of the negative side,
a repeated alternating current waveform combination is provided by a 1st repetitive alternating current waveform pattern providing one level of the two electric potential levels for the time of a 2nd reference time and providing the other level of the electric potential levels for ½ the time of the said 2nd reference time, and
a 2nd repetitive alternating current waveform pattern providing the said one level of electric potential levels for ½ of the time of the said 2nd reference time, providing the aforementioned reference electric potential for ½ of the time of the said 2nd reference time and providing the said other level of electric potential for ½ of the time of the said reference time, and
a pause providing the said electrical potential for ½ of the time of the said 2nd reference time
in the sequence of the said 1st repetitive pattern, the said pause, the said 1st repetitive pattern, the said pause, the said 2nd repetitive pattern, the said pause, the said 2nd repetitive pattern and said pause.

6. A method according to claim 1, for promoting oral hygiene, treating a patient for gingivitis, other periodontal problems, or oral mal odor wherein the said alternating current waveforms are provided with a 1st reference electric potential as a mid-point of the electric potential level on the positive side and the electric potential level on the negative side,
the repeated alternating current waveform combination are provided by a 3rd repetitive alternating current waveform pattern providing one of two electrical potential levels for the time of a 3rd reference time and providing the afore-mentioned other level of the electric potential levels for the time of the said 3rd reference time and providing the other level of the electric potential levels for the time of the said 3rd reference time and providing the said reference electric potential for twice the time of the said 3rd reference time and providing the said other level of the electric potential levels for ¼ of the time of the said 3rd reference time and providing the said reference electric potential for ½ of the time of the said 3rd reference time and providing the said other level of electric potential levels for ¼ of the time of the said 3rd reference time and providing the said reference electric potential for the time of the said 3rd reference time and providing the said other level of the electric potential levels for ¼ of the time of the said 3rd reference time and providing the reference electric potential for ½ of the time of the 3rd reference time and providing the said other level of the electric potential levels for ¼ of the time of the 3rd reference time and providing the said reference electric potential for the time of the said reference time, and a repetitive pattern in one direction providing the said reference electric potential for the time of the said 3rd reference time and providing the said one electric potential level for the ¼ of time of the said 3rd reference time and providing the said reference electric potential for the ½ of time of the said 3rd reference time and providing the said one level of the electric potential levels for the ¼ time of the said 3rd reference time, and a repetitive pattern in the other direction providing the said reference electric potential for the time of the said 3rd reference time and providing the said other level of the electric potential levels for the ¼ of the time of the said 3rd reference time and providing the said reference electric potential for the ½ of the time of the said 3rd reference time and providing the said other level of the electric potential levels for the ¼ of the time of the said 3rd reference time, and a pause providing the said electrical potential for the time of the said 3rd reference time in the sequence of the said 3rd repetitive pattern, the said 3rd repetitive pattern, the said repetitive pattern in one direction, the said repetitive pattern in the other direction, the said pause, the said repetitive pattern in one direction, the said repetitive pattern in the other direction, the said pause, and the said repetitive pattern in one direction.

7. A method according to claim 1 for promoting oral hygiene, treating a patient for gingivitis, other periodontal problems, or oral mal odor, wherein the alternating current waveform is such that it is characterized by the alternating current waveform with:

a 1st reference electric potential as a mid-point of an electric potential level on a positive side and the electric potential level on a negative side, repetitive alternating current waveform combinations are provided by repetitively combining the said alternating current waveforms provided as a single pattern in an alternating current square-wave pattern in a manner such that one level of the two electric potentials is provided and then, in turn, another electric potential is provided for the time of a 1st reference time, and a triple consecutive pattern in which the said single pattern is continued three times, and a pause for twice the time of the said 1st reference time in the sequence of the said triple consecutive pattern, the said pause, the said triple consecutive pattern, the said pause, the said single pattern, the said pause, the said single pattern, the said pause, the said single pattern, the said pause and the said single pattern, the said pause; then a reference electrical potential as a mid-point of the electrical potential level on the positive side and the electric potential level of the negative side, a repeated alternating current waveform combination is provided by a 1st repetitive alternating current waveform pattern providing one level of the two electric potential levels for the time of a 2nd reference time and providing the other level of the electric potential levels for ½ the time of the said 2nd reference time, and a 2nd repetitive alternating current waveform pattern providing the said one level of electric potential levels for ½ of the time of the said 2nd reference time, providing the aforementioned reference electric potential for ½ of the time of the said 2nd reference time and providing the said other level of electric potential for ½ of the time of the said reference time, and a pause providing the said electrical potential for ½ of the time of the said 2nd reference time in the sequence of the said 1st repetitive pattern, the said pause, the said 1st repetitive pattern, the said pause, the said 2nd repetitive pattern, the said pause, the said 2nd repetitive pattern and said pause; then a 1st reference electric potential as a mid-point of the electric potential level on the positive side and the electric potential level on the negative side, the repeated alternating current waveform combination are provided by a 3rd repetitive alternating current waveform pattern providing one of two electrical potential levels for the time of a 3rd reference time and providing the aforementioned other level of the electric potential levels for the time of the said 3rd reference time and providing the other level of the electric potential levels for the time of the said 3rd reference time and providing the said reference electric potential for twice the time of the said 3rd reference time and providing the said other level of the electric potential levels for ¼ of the time of the said 3rd reference time and providing the said reference electric potential for ½ of the time of the said 3rd reference time and providing the said other level of electric potential levels for ¼ of the time of the said 3rd reference time and providing the said reference electric potential for the time of the said 3rd reference time and providing the said other level of the electric potential levels for ¼ of the time of the said 3rd reference time and providing the reference electric potential for ½ of the time of the 3rd reference time and providing the said other level of the electric potential levels for ¼ of the time of the 3rd reference time and providing the said reference electric potential for the time of the said reference time, and a repetitive pattern in one direction providing the said reference electric potential for the time of the said 3rd reference time and providing the said one electric potential level for the ¼ of time of the said 3rd reference time and providing the said reference electric potential for the ½ of time of the said 3rd reference time and providing the said one level of the electric potential levels for the ¼ time of the said 3rd reference time, and a repetitive pattern in the other direction providing the said reference electric potential for the time of the said 3rd reference time and providing the said other level of the electric potential levels for the ¼ of the time of the said 3rd reference time and providing the said reference electric potential for the ½ of the time of the said 3rd reference time and providing the said other level of the electric potential levels for the ¼ of the time of the said 3rd reference time, and a pause providing the said electrical potential for the time of the said 3rd reference time in the sequence of the said 3rd repetitive pattern, the said 3rd repetitive pattern, the said repetitive pattern in one direction, the said repetitive pattern in the other direction, the said pause, the said repetitive pattern in one direction, the said repetitive pattern in the other direction, the said pause, and the said repetitive pattern in one direction.

8. A method according to claim 7 for promoting oral hygiene, treating a patient for gingivitis, other periodontal problems, or oral mal odor, wherein the said 1st reference time is 0.4 second.

9. A method according to claim 1 for promoting oral hygiene, treating a patient for gingivitis, other periodontal problems, or oral mal odor wherein the electrical current waveforms transmitted to the gums of the patient are transmitted thereto from a device comprising an electrical output apparatus providing the electrical current waveforms of electrical voltage within the range of from about ±0.1V to about ±3.9V as a combination of ultra-weak electrical currents that are comprised of a combination of multiple types of current waveforms made up of alternating current square-waves of differing patterns, such that there is applied to the gums a low electrical current of 500µA or less through a pair of disposable electrical conductive elements electrically communicating to said electrical output apparatus and inserted into the oral cavity of the patient and contacting the gums of the patient, said pair of electrical conductive elements containing an electrical conductive amount of an electrical conductive material such that the electrical resistance of the electrical conductive electrical conductive elements is 1 kΩ or less.

10. A method according to claim 9 for promoting oral hygiene, treating a patient for gingivitis, other periodontal problems, or oral mal odor, wherein the electrical current waveforms transmitted to the gums of the patient are electrical current waveforms of electrical voltage within the range of from about ±0.3V to about ±1.3V.

* * * * *